(12) United States Patent
Kienzle et al.

(10) Patent No.: US 6,891,513 B2
(45) Date of Patent: May 10, 2005

(54) ANTENNA SYSTEM FOR A LEVEL MEASUREMENT APPARATUS

(75) Inventors: Klaus Kienzle, Zell (DE); Jurgen Motzer, Gengenbach (DE); Daniel Schultheiss, Hornberg (DE); Josef Fehrenbach, Haslach (DE)

(73) Assignee: Vega Greishaber, KG, Schiltach (DE)

( * ) Notice: Subject to any disclaimer, the term of this patent is extended or adjusted under 35 U.S.C. 154(b) by 170 days.

(21) Appl. No.: 10/304,886

(22) Filed: Nov. 26, 2002

(65) Prior Publication Data

US 2003/0151560 A1 Aug. 14, 2003

Related U.S. Application Data

(60) Provisional application No. 60/333,440, filed on Nov. 26, 2001.

(51) Int. Cl.[7] .......................... H01Q 13/00; H01Q 1/38
(52) U.S. Cl. ................. 343/786; 343/772; 343/700 MS
(58) Field of Search ................................ 343/786, 772, 343/789, 700 MS, 784, 785; H01Q 13/00, 1/38

(56) References Cited

U.S. PATENT DOCUMENTS

| 4,318,103 | A | | 3/1982 | Roettele et al. ........... 343/18 E |
|---|---|---|---|---|
| 5,317,329 | A | | 5/1994 | Hatasa ....................... 343/786 |
| 6,310,574 | B1 | * | 10/2001 | Fehrenbach et al. ........ 342/124 |
| 6,417,748 | B1 | * | 7/2002 | Lopatin et al. ............. 333/252 |
| 6,469,676 | B1 | * | 10/2002 | Fehrenbach et al. ........ 343/786 |
| 6,661,389 | B2 | * | 12/2003 | Griessbaum et al. ........ 343/786 |
| 2002/0121138 | A1 | * | 9/2002 | Malzahn ................... 73/290 R |

FOREIGN PATENT DOCUMENTS

| DE | 94 12 243 | | 11/1994 | ........... G01F/23/28 |
|---|---|---|---|---|
| DE | 198 00 306 | | 7/1999 | .......... H01Q/13/24 |
| EP | 0 882 955 | | 12/1998 | .......... G01F/23/284 |
| JP | 2001-324374 | * | 11/2001 | .......... G01F/23/284 |
| WO | WO 03/085365 A1 | * | 10/2003 | .......... G01F/23/284 |

OTHER PUBLICATIONS

Gregor Gronau, *Introduction to the Theory and Technology of Planar Microwave Antennas to Micro Microstrip Technology*, Progressed High–Frequency Engineering, Bound 3, Nellissen–Wolff, 1990.

Abstract, *Aerial unit for filling level measuring radar unit for radiating microwaves along main radiating direction in container*, German Patent No. DE19800306; Jul. 15, 1999.

Abstract, *Level measuring apparatus using microwaves*, European Patent No. EP0882955; Dec. 9, 1998.

Das et al., *Impedence of a Radiating Slot in the Ground Plane of a Microstripline*, IEEE Transactions on Antennas and Propagation, vol. AP–30, No. 5, Sep. 1982, pps. 922–926.

Pozar et al., *Comments on "Impedence of a Radiating Slot in the Ground Plane of a Microstripline"*, IEEE Transactions on Antennas and Propagation, vol. AP–34, No. 7, Jul. 1986, pps. 958–959.

* cited by examiner

*Primary Examiner*—Don Wong
*Assistant Examiner*—Trinh Vo Dinh
(74) *Attorney, Agent, or Firm*—Wood, Herron & Evans, L.L.P.

(57) ABSTRACT

The present invention relates to an antenna system for a level measuring device for emitting microwaves by means of an antenna horn, at the front side of the small funnel aperture thereof. HF energy in the form of microwave signals is directly axially coupled by means of planar structures having one patch or several patches.

26 Claims, 9 Drawing Sheets

ANTENNA SYSTEM FOR A LEVEL MEASUREMENT APPARATUS

CROSS REFERENCE TO RELATED APPLICATIONS

The present application is a continuation-in-part of U.S. provisional application Ser. No. 60/333,440, filed Nov. 26, 2001, which is expressly incorporated herein, in its entirety, by reference.

FIELD OF THE INVENTION

The present invention relates to an antenna system for a level measuring device suited for the contact-free measurement of filling levels. Such an antenna system is in particular destined for being used with a so-called filling level radar device and a radar level transmitter, respectively. Such devices are also often called radar level sensor. Furthermore, the present invention relates to a filling level radar comprising such an antenna system. In general, antenna systems of the kind mentioned above are used to emit microwave signals. The emission of the microwave signals can be carried out non-continuously or continuously. Non-continuously emitted signals are for example microwave pulses. Radar level sensors emitting continuously microwaves are often called FMCW (frequency modulated continuous wave)-radar level sensors.

BACKGROUND INFORMATION

Antenna systems of that type are mainly used for the measurement of filling levels of filling products of any kind, in particular of bulk goods and fluids in storage tanks or receptacles. The determination of the filling level height thereby ensues by measuring the transit time of a microwave pulse, which is emitted by means of the antenna system into the direction of the surface of the filling level to be determined, is reflected from the surface and received by the antenna system, and which is finally transmitted to a combined emitting and receiving module. Through the signal transit time and the wave propagation speed, the path travelled by the signal and, with knowledge of the receptacle height, the filling level may then be determined. For emitting the microwave pulses necessary for this purpose, horn antennas inter alia are used.

Horn antennas are already known from prior art in the field of the filling level measuring technology; however, all of them exhibit certain problems due to their constructional configuration and length.

The microwaves necessary for the level measurement are generated by a high-frequency module (HF module). According to prior art, these microwave signals are laterally coupled into a waveguide via an exciter pin. The exciter pin, which is in most cases used in conjunction with a glass feedthrough, is thereby fed via a coaxial cable from the HF module. From German utility model DE 94 12 243 U1, a horn antenna is known, having an exciter pin connected to a coaxial cable for the level measurement, which exciter pin engages into the lateral wall of a cup-like metal shell. Following this cup-like metal shell is a waveguide. The waveguide in turn is followed by a thereto coupled antenna horn.

A further development of this arrangement consists in providing a planar structure (patch) instead of the exciter pin, so as to couple in turn the microwave pulses into a waveguide, as well. The planar structure is thereby applied on a dielectric material having a dielectric constant of $\in_1$, and is located on one end of a waveguide. It is proposed in DE 198 00 306 A1, to carry out the coupling of microwaves into a waveguide with the assistance of planar radiation elements. The planar radiation elements are thereby provided on a front end of the waveguide. This solution, however, is again based on the construction-inherent problem that such an antenna system requires a large constructional space—which is mainly extended in the longitudinal direction.

All kinds of feeder systems known, however, have in common that the microwave pulses are coupled into a waveguide, to which follows an antenna horn flaring in the propagation direction. Hereby, the exact matching of the waveguide dimensions to the transmission frequency range of the microwave signal is problematic for allowing only the fundamental mode of wave to propagate within the waveguide. Matching adjustments for the waveguide, which are not exact enough, can lead to signal distortions due to wave dispersion, eventually resulting in a misrepresented measurement result.

SUMMARY OF THE INVENTION

According to a first aspect of the invention an antenna system for a radar level measuring device such as, for example, a level measuring device for measuring a filling level of a filling product in a receptacle, is provided, wherein the antenna system comprises an antenna horn having an inner antenna horn flaring zone, and a planar structure present in the antenna horn flaring zone, which planar structure couples microwave signals into the antenna horn for determining the filling level of the filling product, which microwave signals are then emitted by the antenna horn into the direction of the filling product.

According to a second aspect of the invention, an antenna system for a level measuring device for measuring the filling level of a filling product in a receptacle, comprises an antenna horn having an inner antenna horn flaring zone, and being at least partially filled with a filling of a dielectric material, the dielectric constant of which is greater than or equal to one, and a planar structure present in the antenna horn flaring zone coupling microwave signals into the antenna horn for determining the filling level of the filling product, which microwave signals are then emitted by the antenna horn into the direction of the filling product.

According to another aspect of the invention, an antenna system for a level measuring device for measuring the filling level of a filling product in a receptacle, comprises an antenna horn having a first and a therefrom spaced second horn aperture, of which the second horn aperture has a larger diameter than the first horn aperture, and an antenna horn flaring zone extending in between same, and a planar structure containing at least one patch being present in the antenna horn flaring zone close to the first horn aperture, by means of which patch microwave signals can be directly coupled into the antenna horn for determining the filling level of the filling product, which microwave signals are then emitted by the antenna horn into the direction of the filling product.

Thus, in an inventive antenna system according to one of the above mentioned aspects of the invention, a waveguide is for the first time dispensed of, into which microwave signals have been coupled to date, whereby the longitudinal extension of the antenna system can be reduced. Instead of the waveguide for example a coaxial cable my be connected to the planar structure with for example the at least one patch on it to conduct microwave signals (e.g. microwave pulses)

from a microwave unit of the radar sensor generating microwave signals to the antenna system according to the present invention such that microwaves are emitted in the direction of a product of which the level has to be measured. One advantage of the present invention may be that the antenna system is more compact and is small enough to be used even under very constricted space conditions.

Such as has already been described, it might has been common usage to couple microwaves—either by means of an exciter pin or using patches—into a waveguide followed by an antenna horn. This coupling into a waveguide originally was necessary in a construction-contingent manner due to the lateral arrangement of the exciter pin. With the further development of this system using, instead of the exciter pin, planar structures for coupling in the microwaves, the principle of coupling into a waveguide was maintained, since the experts thought that this would be necessary for a perfect function of the system.

The combination of a waveguide and an antenna horn, however, required an important component extension in the longitudinal direction. Surprisingly, it was found after conducting extensive tests that it is possible to couple HF energy in the form of microwaves by means of a planar structure (patch) directly into an antenna horn, e.g. in the zone of the horn flaring. According to an exemplary embodiment of the present invention planar structures with two or four, may even more rectangular patches optimized for a frequency of 26 GHz have turned out to be particularly suited. The hereby used patches can also have any other shapes, such as, for example, triangular, oval or circular shapes. For enabling a direct coupling, the patches may be arranged directly at the antenna horn front end. Through this direct coupling into the antenna horn, the constructional length of the antenna system is reduced by up to 60% as compared to conventional systems. The length of a prior art 2" antenna with a waveguide at a frequency of 26 GHz, for example, is about 160 mm, whereas the configuration of the novel claimed features is only 65 mm at comparable electric properties.

Antennas are often used in chemically aggressive environmental conditions or in the food sector. For protecting the patches from a possible chemical action or from getting dirtied by foodstuffs, inventive antenna systems are preferably filled completely or in part with a dielectric material. This filling with a dielectric material (e.g. PP, PVDF, PTFE, ceramic or mixtures thereof) having a dielectric constant of $\in_2 \geq 1$, apart from the protection from a chemical action and a dirtying of the patch, has also a mechanically abrasive protective effect, which can be very useful with certain filling products. Moreover, it is to be stated here that by filling the horn antennas with a dielectric material, the condensate is at the same time prevented from penetrating into the inner antenna space.

Filling the antenna with a dielectric material, however, serves a completely different purpose: apart from the purely protective effect resulting for the antenna, the use of such a filling allows for further reducing the size of the antenna system in that the radiation surface of the filling is given the form of an optical lens or a cone, whereby the wave propagation angle can be reduced. This corresponds simultaneously to the achievement of a higher gain of an inventive antenna system as compared to a conventional antenna having altogether the same properties. Apart from the plain advantage of achieving a higher gain, the use of a dielectric filling medium thus allows for the size reduction of the antenna: By the fact that due to the lens or cone form of the filling medium the wave propagation angle is reduced and the wave signal is therewith less scattered than it is usual with patch antennas, the number of the necessary patches can be reduced for achieving a determined predefined gain. This, however, in turn entails a reduction in the antenna size—above all in the diameter thereof.

Thus, by focussing the free-space wave coupled in by the patches effected by the antenna horn and the dielectric material present in the antenna horn, the reduction of the number of patches required for achieving a certain gain may be possible. Preferably, four separate patches are used, which are electrically coupled to each other. Hence, it is likewise possible to use only one, two, or more than four patches.

Such an arrangement of more than one patch may represent a further advantage of the invention: If it was hitherto possible to use a single patch for coupling in signals due to the very small diameter of the waveguide, the possibility is now offered thanks to the invention of using more than only one patch, since the diameter of the antenna horn at the respective frequency is distinctly larger than the hitherto necessary waveguide diameter. By using several patches, the gain can therewith be distinctly increased, resulting in an increased measurement accuracy.

It may moreover very advantageous that inventive antenna systems may be produced at low expenditure and therefore in a very cost-efficient manner. Due to the minor component dimensions, smaller housings, as well as enclosures are possible.

Another advantage of the invention may reside in that an antenna system of that kind can even be used in very high frequency ranges. In the frequency range of over 30 or 50 GHz, the mechanical dimensions of a waveguide usually become so small that a conventional construction can no longer be operated.

Another important advantage may be represented by the system-contingent explosion-proof isolation of this construction. Thus, in hazardous environmental conditions, no extra care has to be taken for the explosion-proof isolation since the separate grounding necessary for this purpose (circuit mass, ground) is already given system-contingently. The isolation of the circuit mass relative to the receptacle mass thus ensues with the present invention by means of the circuit board on which the patches are located. The patches are hereby connected with the circuit mass via the inner conductor of the coaxial cable.

The present invention moreover turns out to be particularly advantageous in that apart from the coaxial feeding of the patches, all other conventional methods, such as, for example, the microstrip, the microstrip-sandwich, the slot or coplanar feeding method is possible.

Such as has already been explained at the beginning of the representation of the invention, there exists a certain demand for antenna systems being made available, which are small enough to be used even in very constricted space conditions. This demand for such miniaturized antenna systems can be complied with by means of the invention. Thus, the inventive antenna systems can also be used in receptacles having a very low height, the receptacle volumes of which shall be fully used.

According to a further aspect of the invention an exemplary embodiment of an antenna system of the present invention comprises an antenna horn having an inner antenna horn flaring zone, and a planar structure present at one end of the antenna, which planar structure couples microwave signals into the antenna horn for determining the filling level of the filling product.

In an exemplary embodiment of an antenna system of the present invention mentioned above the planar structure comprises at least one patch.

In a further exemplary embodiment of an antenna system of the present invention mentioned above, the inner antenna horn flaring zone is at least in part filled with a filling of a dielectric material of a dielectric constant of greater than or equal to one. The filling material may be chosen from the group comprising PP, PTFE and ceramic.

In a further exemplary embodiment of an antenna system of the present invention mentioned above, the antenna system comprises furthermore a wafer of a dielectric material transmissive for microwaves, wherein the wafer being arranged in front of the planar structure and being sealed within the inner antenna horn flaring zone.

In a further exemplary embodiment of an antenna system of the present invention mentioned above, the antenna horn has a first horn aperture and a second horn aperture of which the second horn aperture having a greater diameter than the first horn aperture, and the wafer being arranged next to the second horn aperture.

In a further exemplary embodiment of an antenna system of the present invention mentioned above, the wafer has a certain thickness (t) of about λ/2 divided by the square root of the dielectric constant $\in_r$ of the dielectric material of the wafer and multiplied with n, wherein λ is the wavelength of the microwaves to be emitted by the antenna system, and n∈N*. The corresponding formula is:

$$t = \frac{\lambda}{2 * \sqrt{\varepsilon_r}} * n$$

BRIEF DESCRIPTION OF THE DRAWINGS

Several exemplary embodiments of the present invention are described in the following with reference to the attached drawings of which:

FIG. 5 shows in the embodiments a through c various possible antenna horn shapes with which the inventive antenna systems can be equipped;

FIG. 6 shows in the embodiments a through f various antenna horn fillings with various possible lens forms with which the inventive antenna systems can be equipped;

FIG. 7 shows in the embodiments a through j various antenna horn filling forms with which the inventive antenna systems can be equipped.

DESCRIPTION OF EXEMPLARY EMBODIMENTS OF THE PRESENT INVENTION

Figure 1:
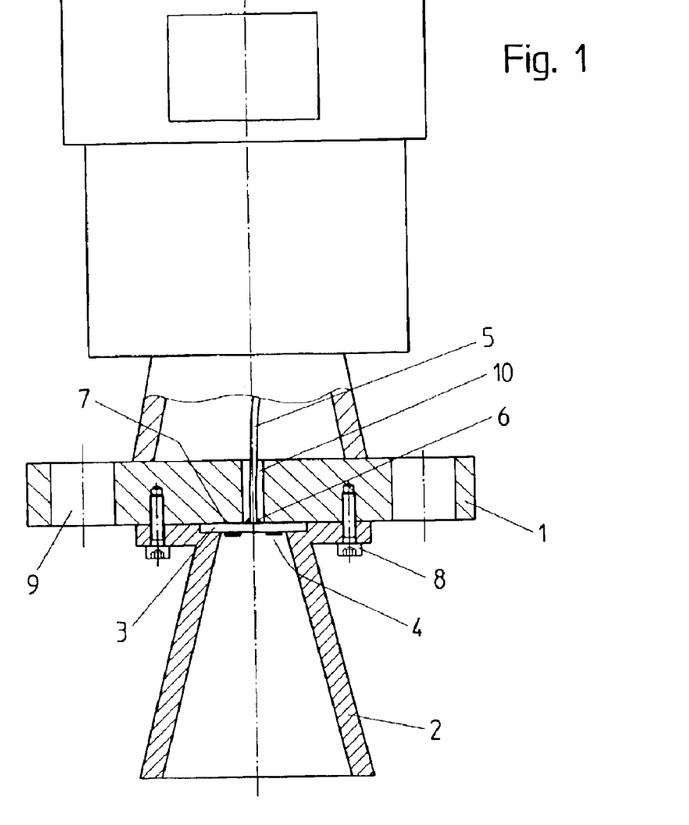
FIG. 1 is a partial longitudinal cut through a first embodiment of the invention.

FIG. 1 is a longitudinal cut through an inventive antenna system. The antenna system is comprised of a metallic flange 1, which is provided with a plurality of bores 9. The bores 9 serve for receiving screws by means of which the antenna system is to be attached on a receptacle or storage tank (not shown) having an aperture through which the metallic antenna horn 2 protrudes into the inner receptacle space. The bores 9, for this purpose, have to find their continuation in corresponding bores in the receptacle wall, so as to allow the antenna system to be screwed with the receptacle. Moreover, flange 1 has a further bore 10 in its center, through which a coaxial cable 5 is guided. Below flange 1 of the antenna system, an antenna horn 2 is attached with screws 8.

The antenna horn 2 is fixed on flange 1 in such a manner that the center axis of the antenna horn 2 is coaxial to the center axis of bore 10. Antenna horn 2 features a recess at the front side of its small funnel opening. In the recess, a substrate 3 is clamped between flange 1 and antenna horn 2. The substrate 3 serves as a carrier material for the patches 4 present thereon. Between substrate 3 and flange 1, a thin continuous ground surface 7 is arranged.

The patches 4 arranged on the lower side of substrate 3 are situated directly at the front side of the small antenna horn aperture. The patches 4 are supplied with HF energy via coaxial cable 5. The HF signal in turn is generated by a HF module (not shown), and is fed to the patches 4 present on substrate 3 via coaxial cable 5. Coaxial cable 5 thereby can be fixed on either sides of the HF module, as well as on substrate 3, either by means of a soldering joint 6 or a plug connection.

Substrate 3 consists of a dielectric material constituting inter alia an explosion-proof isolation. The continuous ground surface 7, as well as the dielectric substrate 3, are clamped by antenna horn 2 onto flange 1 in such a manner that the planar normal of substrate 3 coincides with the main wave propagation direction A.

Figure 2:
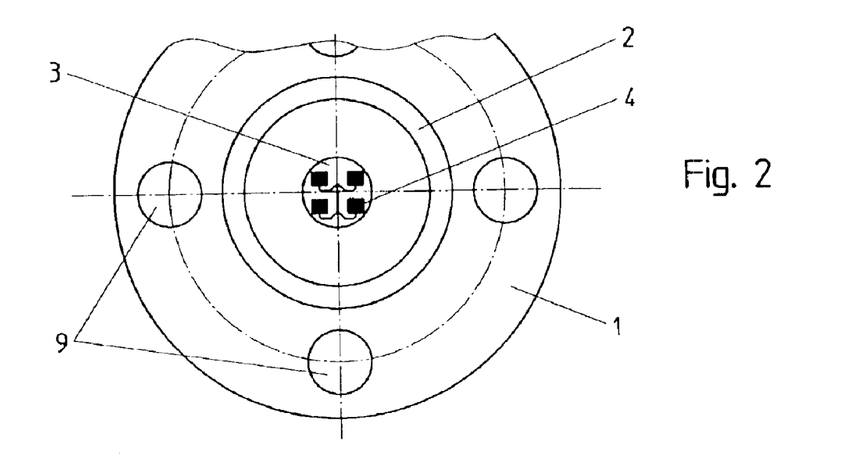
FIG. 2 shows a view of FIG. 1 from below, in the reverse direction of the main wave propagation direction A.

In FIG. 2, the antenna system of FIG. 1 is shown in a view from below. Hereby, the concentric arrangement of the essential components can be seen. Four separate patches 4 can be seen here arranged on substrate 3 concentrically to the main wave propagation direction A. The four patches 4 are electrically coupled with each other.

Figure 3:
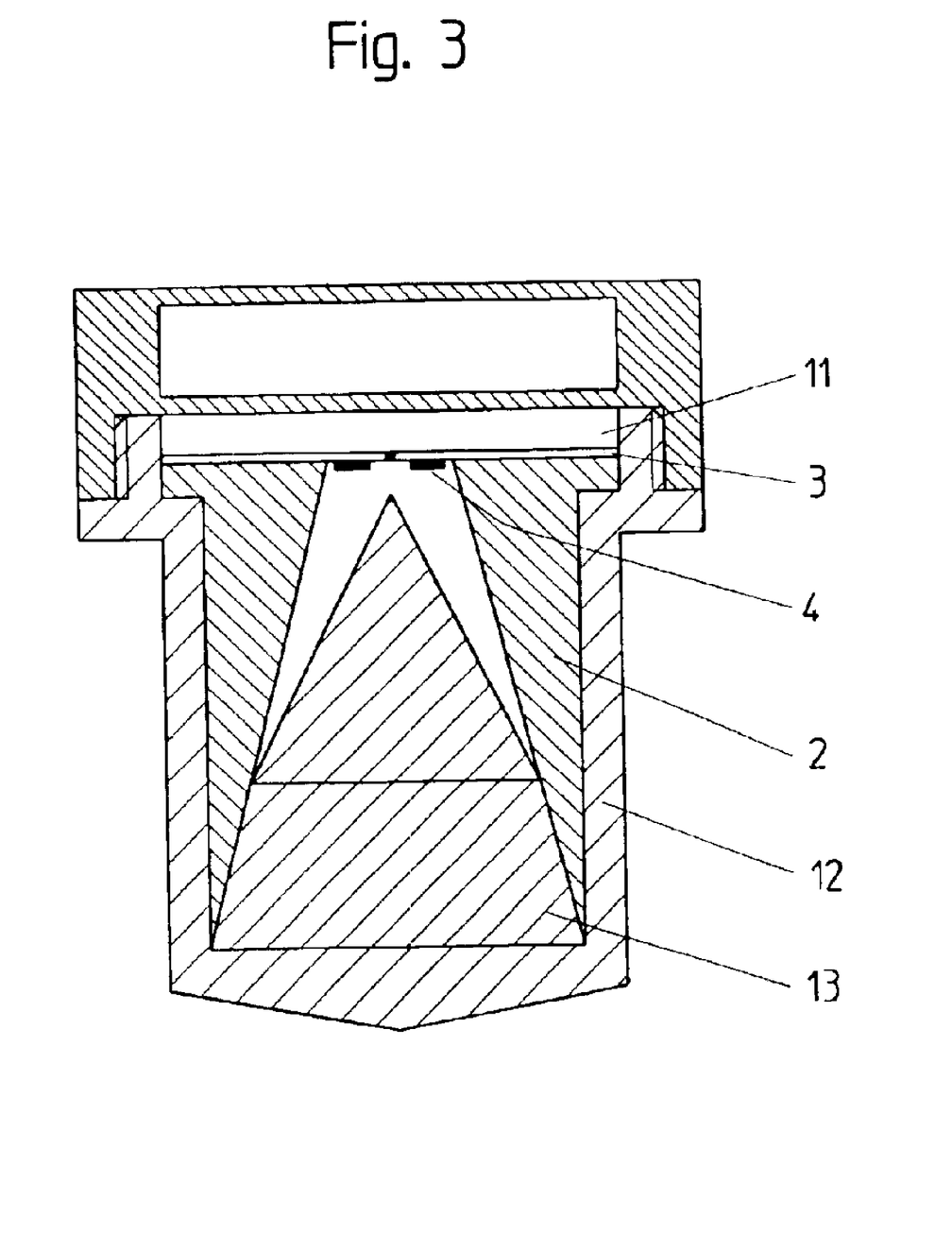
FIG. 3 is a longitudinal cut of another embodiment of the invention.

FIG. 3 shows another embodiment of the invention. The antenna system here, as well, is comprised of an antenna horn 2, into the smaller opening of which HF signals are coupled via patches 4 present directly at the front side of the smaller antenna horn aperture. The planar geometry of the patches 4 is present on a dielectric substrate 3. In the embodiment described in FIG. 3, the wiring between the HF module and the antenna system can be omitted. This is achieved in that the patches 4 are seated on the same printed circuit board as the active components of HF module 11 or are connected with HF module 11 by means of a through-plating on a multilayer board.

Moreover, a filling 13 and an enclosure 12 of the metallic horn antenna 2 is shown in FIG. 3. The enveloping surface of the metallic antenna horn 2, for one, is completely surrounded by an enclosure 13 of a dielectric material, e.g. PVDF. For another, the hollow space formed by antenna horn 2 is completely or at least in part filled with a dielectric material, e.g. PP. Filling 13 thereby can have various shapes. The possible filling shapes are explained in the other Figures.

Figure 4:
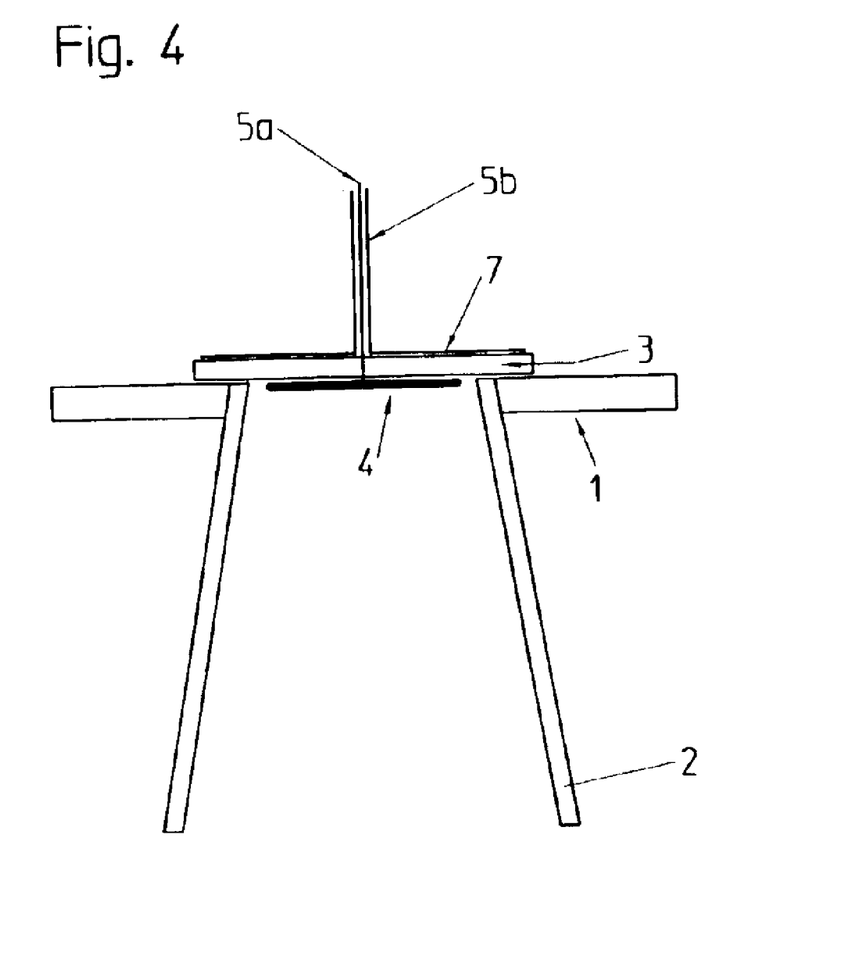
FIG. 4 is a schematic drawing, in which the principle of the explosion-proof isolation can be seen.

As has already been mentioned, an important advantage of this construction resides in that the separate conductivity to ground necessary for the explosion-proof isolation is already given in a system-contingent manner. In the schematic drawing of FIG. 4, this explosion-proof isolation is shown in an example. In the present invention, the isolation from the receptacle ground of the circuit mass of the HF module, which is connected with the antenna via the outer conductor of coaxial cable 5b, ensues by a coupling to the metallic antenna horn 2 through substrate 3 on which the patches 4 are applied. The thickness of substrate 3 is selected in accordance with the voltage stability of the explosion-proofness requirements (e.g. 0.5 mm). In the HF module, the isolation of the inner conductor 5a of the coaxial cable from the outer conductor 5b takes place, as well.

Figure 5A:
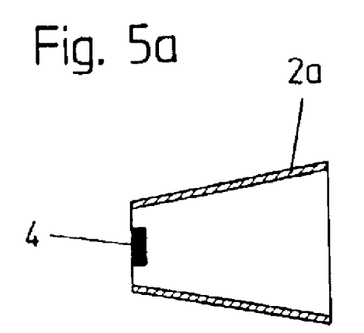
Figure 5B:
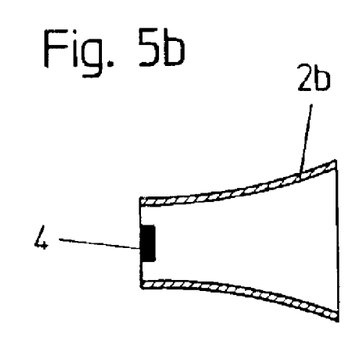
Figure 5C:
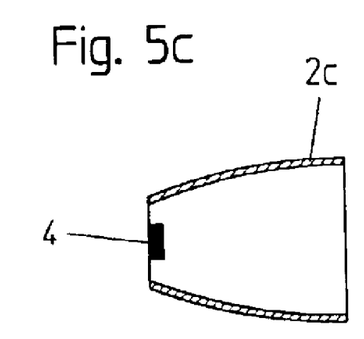
Figure 6A:
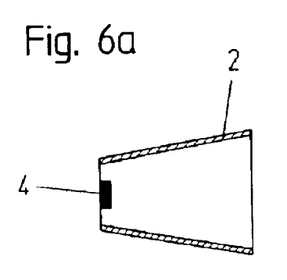
Figure 6B:
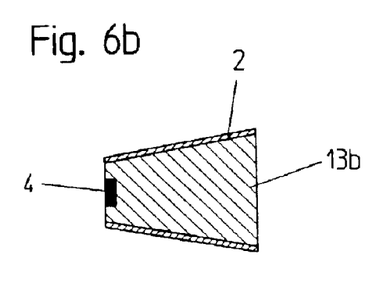
Figure 6C:
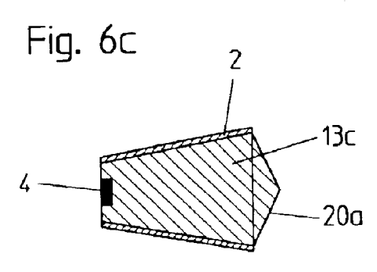
Figure 6D:
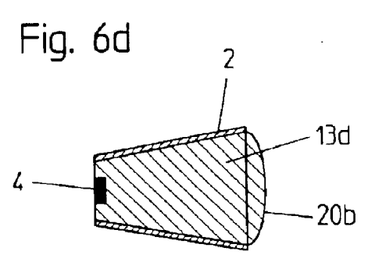
Figure 6E:
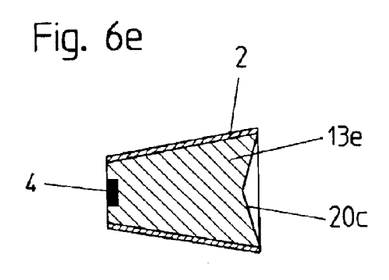
Figure 6F:
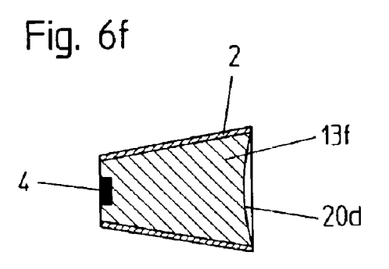
Figure 7A:
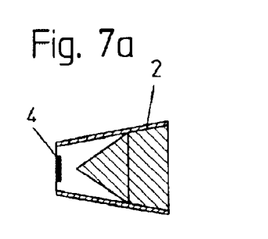
Figure 7B:
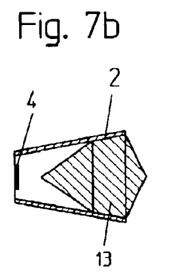
Figure 7C:
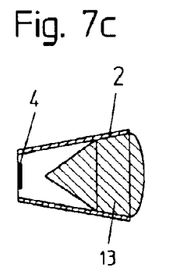
Figure 7D:
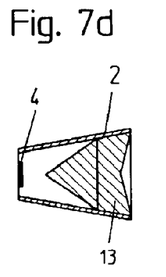
Figure 7E:
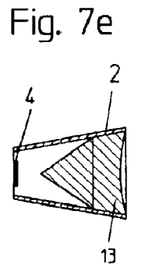
Figure 7F:
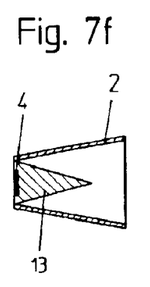
Figure 7G:
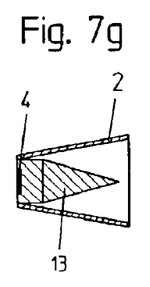
Figure 7H:
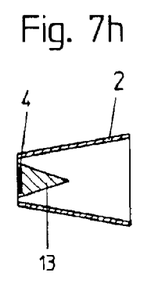
Figure 7I:
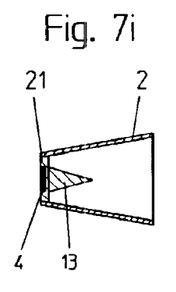
Figure 7J:
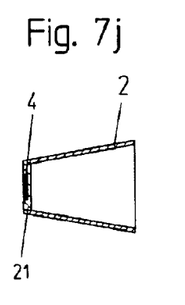

In FIG. 5, various antenna horn shapes 2a, 2b and 2c are shown with which an inventive antenna system can be equipped. The horn shape 2a of FIG. 5a represents the standard horn shape. In addition, however, the trumpet shape 2b shown in FIG. 5b, a convex horn, as well as the tulip form 2c shown in FIG. 5c, hence a concave horn, are likewise used. The number of the mentioned horn shapes 2, 2b and 2c is not restricting. Further horn shapes are moreover possible. Of course, even a combination of the various horn shapes of FIGS. 5a through 5c is imaginable.

In FIG. 6, the essential horn filling shapes 20a–20d are shown. FIG. 6a represents a horn 2 without any filling. The horn 2 shown in FIG. 6b is completely filled with a dielectric material 13b (e.g. PP, PVDF or PTFE), the filling 13b in each case terminating in a planar manner with the front and rear horn aperture end. In FIGS. 6c through 6f, possible lens forms 20a–20d of the fillings 13c–13f are shown. The positive lens forms 20a, 20b of FIGS. 6c and 6d can be configured as circular cones (FIG. 6c), the tip of which pointing into the wave radiation direction, or as a convex lens (FIG. 6d). The negative lenses 20c, 20d of FIGS. 6e and 6f have the shape of a negative cone (FIG. 6e), the tip of which pointing into the reverse wave propagation direction, or a concave form (FIG. 6f).

Various forms of a filling 13 of dielectric material are shown in FIG. 7. All these exemplary embodiments of the present invention can be combined with a planar structure as mentioned above. An exemplary filling material is e.g. PP, PVDF or PTFE. Such a filling 13 can, as has already been mentioned, fill an antenna horn 2 completely or only in part. Hereby, various filling forms are possible. These are shown in the FIGS. 7a through 7j. The filling 13 of FIGS. 7a through 7e are partial fillings, which are only present in the horn front area. In the inner horn space, the filling forms a circular cone, the tip of which pointing into the direction of the smaller horn aperture. The wave radiation surface in the zone of the larger horn aperture can feature various forms. These horn forms possess lens qualities as have already been explained for FIG. 6. The horn filling forms of FIGS. 7f through 7i are partial fillings only present in the rear horn area. The filling forms are in each case comprised of a circular cylinder, the tip of which pointing into the direction of the larger horn aperture. FIG. 7j represents a further embodiment, wherein the patches are simply covered by a planar disk 21 of dielectric material.

All of the horn filling forms shown here serve, on the one hand, for focusing microwaves and, on the other hand, for protecting the patches 4 from actions caused by aggressive environmental conditions or from mechanical impacts caused by bulk goods. The important advantage achieved by focusing microwaves consists in the possibility of optimizing the so-called gain of the antenna.

Apart from the variants shown in FIGS. 5 through 7, all combinations of the various variants are possible for the horn shapes and horn filling variants, i.e. each antenna horn 2 can be combined with each filling 13 and each lens.

Figure 8A:
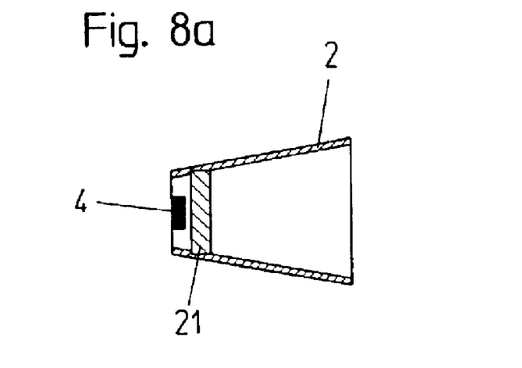
FIGS. 8a–8c show various antenna horn filling forms combined with a circular plate or wafer with which the inventive antenna system can be equipped.
Figure 8B:
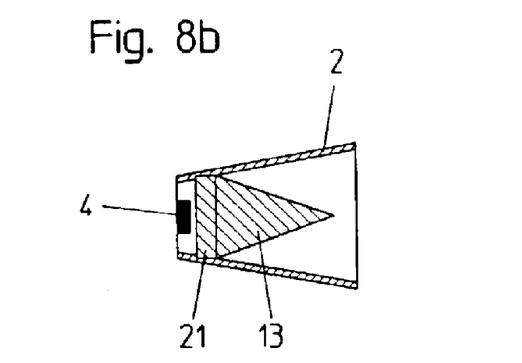
Figure 8C:
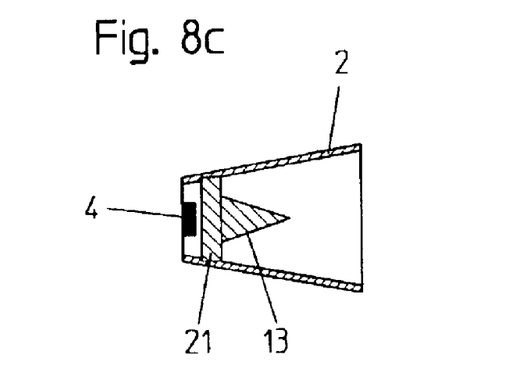

FIGS. 8a–8c show various exemplary embodiments of a filling 13 combined with a wafer 21 within an antenna horn 2 of an inventive antenna system. The wafer 21 shown in FIG. 8a is made of a dielectric material transmissive for microwave signals to be emitted. The wafer 21 is tightly fitted within the antenna horn 2. A planar structure 4 is arranged at the left side of the wafer 21 such that it is protected against for example a chemical aggressive atmosphere within a storage tank in which the antenna horn 2 is directed.

The exemplary embodiment of an antenna system according to the invention shown in FIG. 8b corresponds to the embodiment shown in FIG. 8a except that it is combined with a filling 13 having a conical shape. The tip of the cone shaped filling 13 is directed to a surface of a product of which the level has to be measured. A modification of the embodiment of FIG. 8b is shown in FIG. 8c. Here, a filling 13 combined with a wafer 21 has a base smaller than the base of the cone shaped filling 13 of FIG. 8b. The embodiment according to FIG. 8b as well as the embodiment shown in FIG. 8c of an inventive antenna system may have the advantage that a patch structure 4 is protected against aggressive atmosphere and the emitted radiation can be focused in a desired manner.

Figure 9A:
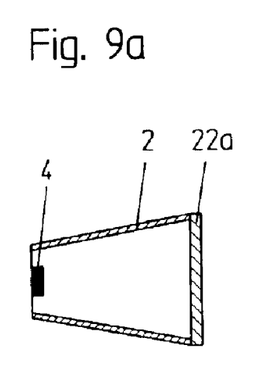
FIGS. 9a–9e show further exemplary embodiments of a wafer next to a front end of a horn antenna.
Figure 9B:
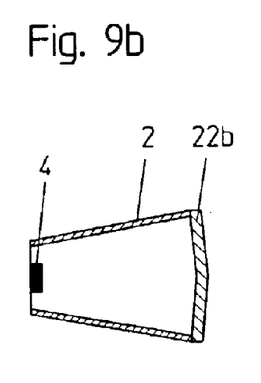
Figure 9C:
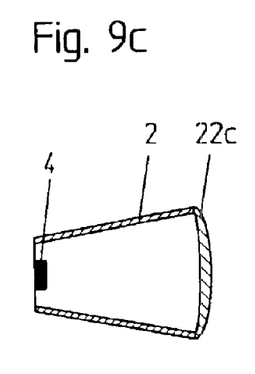
Figure 9D:
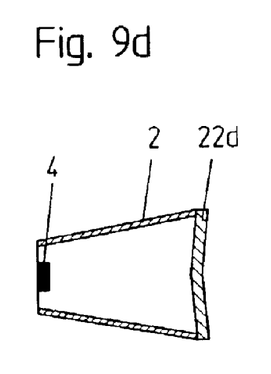
Figure 9E:
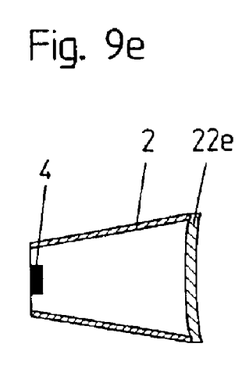

FIGS. 9a–9e show further exemplary embodiments of a combination of an antenna horn 2 and a protection element 22a–e arranged at the second horn aperture of the antenna horn 2. The exemplary embodiment shown in FIG. 9a comprises a protection plate 22a having a planar inner surface and a planar outer surface. The further exemplary embodiment shown in FIG. 9b comprises a protection plate 22b formed in a convex shape. The alternative embodiment according to FIG. 9c comprises a protection plate 22c having a convex shape 2, but the outer surface is rounded. A further modification of a protection plate 22d is shown in FIG. 9d. This protection plate 22d has a concave shape identical with the shape of the modification of FIG. 9b but the tip of the plate 22d is directed to the patch structure 4. Last but not least, a further exemplary embodiment of a concave protection plate 22e is shown in FIG. 9e. Here, the protection plate 22e is identical to the protection plate 22c of FIG. 9c but turned around.

In all exemplary embodiments according to FIGS. 9a–9e the thickness of the protection plate 22a–22e corresponds to a value calculated by $\lambda/2$ divided by the square root of the dielectric constant of the material of the protection plate 22a–22e. The thickness of the protection plate 22a–22e could also be a multiple of the above-mentioned value.

Figure 10:
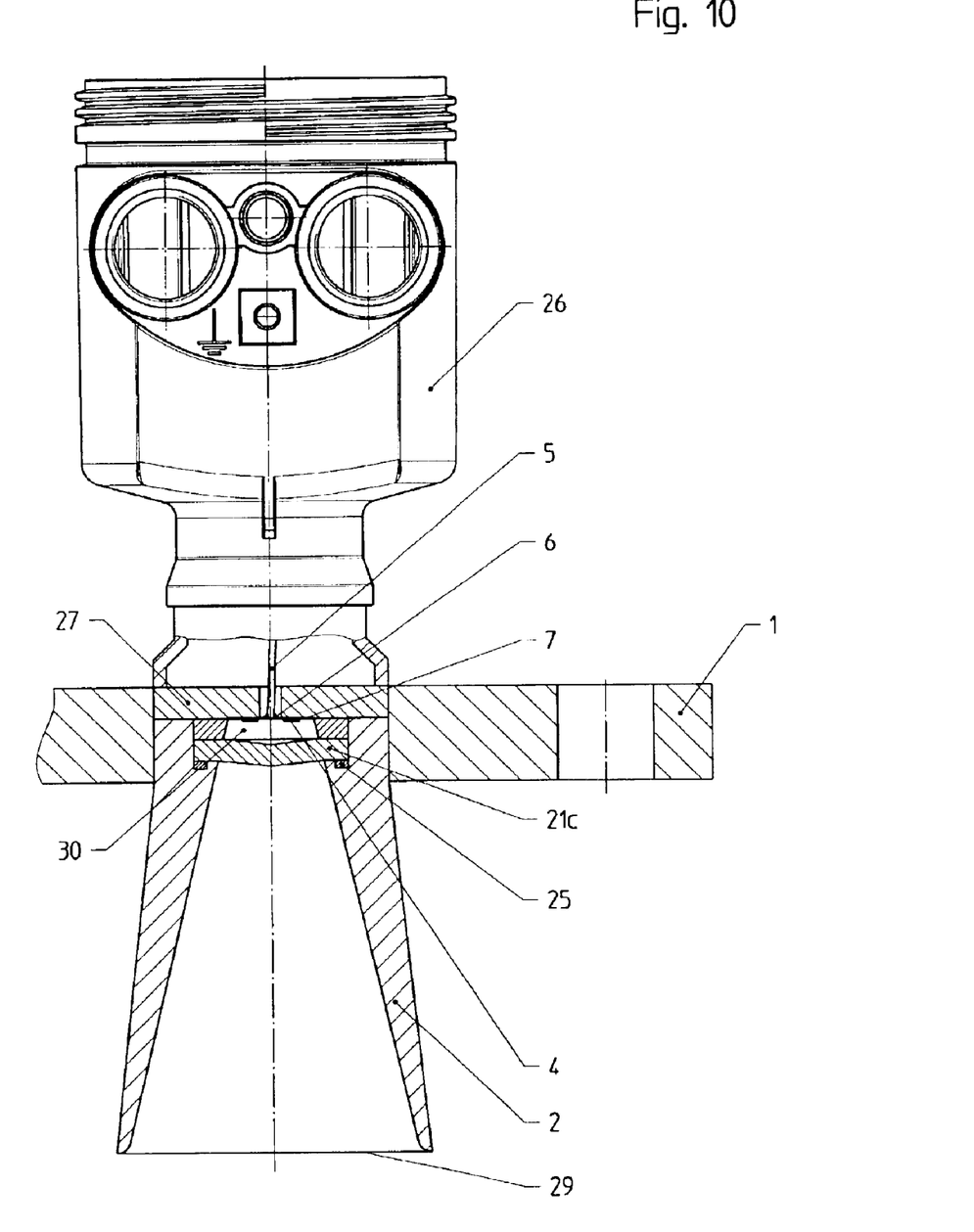
FIG. 10 shows a schematic drawing, partially cut out, of an exemplary embodiment of the present invention, in particular a level transmitter comprising a antenna horn with a planar structure protected by a wafer or disc arranged within the antenna horn.

Finally, a further exemplary embodiment of an inventive antenna system is shown in FIG. 10 in a longitudinal section. Here, a radar level transmitter comprises a housing 26 and an inventive exemplary embodiment of the antenna system. Within the housing 26, inter alia an electronic unit or module is accommodated. The electronic module generates microwave signals, for example microwave pulses. As the electronic units and modules of a radar level transmitter or radar level sensor are well known to a skilled person, detailed explanations with respect to these units are omitted. The module generating microwave pulses is connected with an end of a coaxial cable 5. The other end of the coaxial cable 5 is soldered (position 6) with a planar structure 4 having at least one patch. As an alternative, the coaxial cable 5 could also be electrically connected with the planar structure 4 by a plug-in connection.

The planar structure 4 with the at least one patch is supported in the center of a support disc 27. This support disc 27 abuts against an end face of an antenna horn 2. The antenna horn 2 as shown in FIG. 10, has an aperture 29. Between the end face at which the planar structure 4 is arranged, and the aperture 29 of the antenna horn 2, a protection disc or protection window 21c as mentioned above is arranged. This protection window 21c has a slightly conical section shape of which the tip is directed to the second aperture 29 of the antenna horn 2. For a better sealing between the protection window 21c and the antenna horn 2 a seal ring 25 is fitted within a accommodation groove formed within the antenna horn 2. The whole arrangement, that is the radar level sensor with the antenna is mounted within a hole of a flange 1. This flange 1 acts as a mounting means for the radar level sensor. The flange 1 will be mounted at a storage tank by bolts (not shown).

In operation, the electronic unit generates a microwave pulse which will be conducted by the coaxial cable 5 directly to the planar structure 4. By means of the patches on the planar structure 4, this microwave pulse will be emitted in the direction to the protection window 21c, transmits through the window 21c and maybe focused by the lens shape of that protection plate 21c. By means of the antenna horn 2 the microwave pulse will be sent to a surface of a product to be measured. An echo reflected by the surface of the product is received within the antenna horn 2, transmits through the protection window 21c and will be received by means of the patch or the patches on the planar structure 21c. The reflected echo of the microwave pulse is than conducted by the coaxial cable 5 to the electronic unit within the housing 6 to determine the traveling time. After carrying out various calculations the level is determined and a corresponding signal representing the level of the product within the storage tank is sent to a receiver (not shown).

Finally, it is to be noted that the material of the protection window 21c is transmissive for microwaves and might be covered by a protection coating taking into consideration a potential aggressive atmosphere within the tank.

What is claimed:

1. An antenna system for a level measuring device for measuring a filling level of a filling product in a receptacle by means of microwave signals, comprising an antenna horn having an inner antenna horn flaring zone, and a planar structure present in the inner antenna horn flaring zone, which planar structure couples microwave signals into the antenna horn for determining the filling level of the filling product, which microwave signals are then emitted by the antenna horn.

2. The antenna system of claim 1, wherein the planar structure comprises a single patch.

3. The antenna system of claim 1, wherein the planar structure comprises a plurality of patches, which are electrically coupled with each other.

4. The antenna system of claim 1, wherein the antenna horn comprises a first and a second horn aperture, the second horn aperture being spaced apart from the first horn aperture and comprising a larger diameter than the first horn aperture, and the first horn aperture being connected with an antenna flange and being coaxially arranged to said antenna flange.

5. The antenna horn of claim 1, wherein the antenna horn comprises a first and a second horn aperture, the second horn aperture being spaced from the first horn aperture and comprising a larger diameter than the first horn aperture, and the first horn aperture being connected with an antenna flange and being coaxially arranged to said antenna flange, and the planar structure being arranged at the front side of the first horn aperture.

6. The antenna system of claim 5, wherein the planar structure comprises a single patch.

7. The antenna system of claim 6, wherein the patch is arranged on planar dielectric carrier material and is present in the first horn aperture for coupling the microwaves via same directly into the antenna horn, the planar normal of the carrier material being in parallel to a planar normal of the flange and a center axis of the horn antenna.

8. The antenna system of claim 5, wherein the planar structure comprises a plurality of patches, which are electrically coupled with each other.

9. The antenna system of claim 8, wherein the patches are arranged on a planar dielectric carrier material and are present in the first horn aperture for coupling the microwaves via same directly into the horn antenna, the planar normal of the carrier material being in parallel to a planar normal of the flange and a center axis of the horn antenna.

10. The antenna system of claim 1, wherein the inner antenna horn flaring zone is at least in part filled with a filling of a dielectric material of a dielectric constant of greater than or equal to one.

11. The antenna system of claim 10, wherein the filling is chosen from the group comprising PP, PVDF, PTFE, ceramic and mixtures thereof.

12. The antenna system of claim 1, wherein the antenna system comprises furthermore a wafer of a material transmissive for microwaves, wherein the wafer being arranged in front of the planar structure and being sealed within the inner antenna horn flaring zone.

13. The antenna system of claim 12, wherein the antenna horn has a first horn aperture and a second horn aperture of which the second horn aperture having a greater diameter than the first horn aperture, and the wafer being arranged next to the first horn aperture.

14. The antenna system of claim 12, wherein the wafer has a certain thickness of .lambda./2 divided by the square root of the dielectric constant of the dielectric material of the water and multiplied with n, wherein .lambda. is the wavelength of the microwaves to be emitted by the antenna system, and n.di-elect cons.N*.

15. An antenna system for a level measuring device for measuring a filling level of a filling product in a receptacle, comprising an antenna horn having an inner antenna horn flaring zone and being at least in part filled with a filling of a dielectric material of a dielectric constant of greater than or equal to one, and a planar structure present in the antenna horn flaring zone, which planar structure couples microwave signals into the antenna horn for determining the filling level of the filling product, which microwave signals are then emitted by the antenna horn.

16. The antenna system of claim 15, wherein the dielectric constant of the filling having a value between one and ten.

17. The antenna system of claim 16, wherein the dielectric constant of the filling having a value from 2 to 4.

18. The antenna system of claim 17, wherein the dielectric constant of the filling having a value of approximately 2.2.

19. The antenna system of claim 17, wherein the planar structure comprises at least one patch, and the patch is arranged on a planar dielectric carrier material, and is present at a first horn aperture for coupling via same the microwaves directly into the horn antenna, the planar normal of the carrier material being in parallel to a planar normal of the flange and a center axis of the horn antenna.

20. The antenna system of claim 19, wherein the dielectric constant of the carrier material is greater than the dielectric constant of the filling.

21. The antenna system of claim 15, wherein the antenna horn has a first and a second horn aperture, the second horn aperture having a greater diameter than the first horn aperture, and wherein the filling at the second horn aperture has a radiation surface having the form of an optical lens.

22. The antenna system of claim 21, wherein the form of the optical lens has a concave shaping.

23. The antenna system of claim 21, wherein the form of the optical lens has a convex shaping.

24. A filling level radar device for measuring the level of a filling product in a receptacle by means of microwave signals, comprising a module for generating microwave signals, an antenna horn coupled with the module and having a first and a second horn aperture spaced from the first horn aperture, the second horn aperture having a larger diameter than the first horn aperture, an antenna horn flaring zone extending between the first and the second horn apertures and a planar structure present in the antenna horn flaring zone, the planar structure including at least one patch arranged at the first horn aperture by means of which the microwave signals are directly coupled into the antenna horn for determining the filling level of the filling product, which microwave pulses are then emitted by the antenna horn.

25. The filling level radar device of claim 24, wherein the antenna horn is at least in part filled with a filling of a dielectric material, the dielectric constant of which is greater than or equal to one.

26. A method for emitting microwave signals for determining the filling level of a filling product, the microwave signals being fed into a planar structure for being subsequently coupled by the planar structure directly into an antenna horn, and for being emitted from there into the direction of the filling product.

* * * * *